United States Patent
Mudge et al.

(10) Patent No.: US 11,523,797 B2
(45) Date of Patent: Dec. 13, 2022

(54) VITAL SIGN DETECTION AND MEASUREMENT

(71) Applicant: Welch Allyn, Inc., Skaneateles Falls, NY (US)

(72) Inventors: Kenzi L. Mudge, Skaneateles, NY (US); David E. Quinn, Auburn, NY (US); Henry Joe Smith, III, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 92 days.

(21) Appl. No.: 16/845,878

(22) Filed: Apr. 10, 2020

(65) Prior Publication Data

US 2020/0330068 A1    Oct. 22, 2020

Related U.S. Application Data (60) Provisional application No. 62/834,635, filed on Apr. 16, 2019.

(51) Int. Cl.
*A61B 8/08* (2006.01)
*A61B 8/00* (2006.01)

(52) U.S. Cl.
CPC .............. *A61B 8/08* (2013.01); *A61B 8/4236* (2013.01); *A61B 8/4281* (2013.01);
(Continued)

(58) Field of Classification Search
None
See application file for complete search history.

(56) References Cited

U.S. PATENT DOCUMENTS 4,122,427 A   10/1978   Karsh
4,306,567 A   12/1981   Krasner
(Continued)

FOREIGN PATENT DOCUMENTS

EP   0143046 A2   5/1985
EP   1731101 A1   12/2006
(Continued)

OTHER PUBLICATIONS

European Search Report, EP 20 16 9948, dated Jun. 9, 2020, 8 pages.
(Continued)

*Primary Examiner* — Angela M Hoffa
*Assistant Examiner* — Younhee Choi
(74) *Attorney, Agent, or Firm* — Merchant & Gould P.C.

(57) ABSTRACT

An example monitoring device for detecting and measuring a vital sign of a subject includes: a base; a battery mounted to the base; first and second transceivers attached to the base at opposing angles, and powered by the battery to transmit pulses and receive reflected pulses; an antenna powered by the battery, and configured to wirelessly transmit data acquired from the first and second transceivers; and a computing device powered by the battery, and operatively coupled to the first and second transceivers and the antenna, the computing device having a processing device and a memory storing instructions that, when executed by the processing device, cause the monitoring device to determine a respiration rate by detecting a cyclical change in distance based on the reflected pulses.

12 Claims, 6 Drawing Sheets

(52) U.S. Cl.
    CPC ............ *A61B 8/5223* (2013.01); *A61B 8/543* (2013.01); *A61B 8/56* (2013.01); *A61B 2560/0214* (2013.01)

(56) References Cited

U.S. PATENT DOCUMENTS

| | | | |
|---|---|---|---|
| 4,696,307 A | 9/1987 | Montgieux | |
| 4,872,599 A | 10/1989 | Hubbard et al. | |
| 4,967,751 A | 11/1990 | Sterzer | |
| 5,588,439 A | 12/1996 | Hollub | |
| 5,638,824 A | 6/1997 | Summers | |
| 5,853,005 A | 12/1998 | Scanlon | |
| 5,944,680 A | 8/1999 | Christopherson et al. | |
| 6,893,404 B2 | 5/2005 | Ragnarsdottir | |
| 7,041,062 B2 | 5/2006 | Friedrichs et al. | |
| 7,247,139 B2* | 7/2007 | Yudkovitch | A61B 8/467 704/275 |
| 8,926,509 B2 | 1/2015 | Magar et al. | |
| 2002/0068871 A1* | 6/2002 | Mendlein | A61B 8/4281 600/459 |
| 2004/0097823 A1 | 5/2004 | Friedrichs et al. | |
| 2004/0167389 A1* | 8/2004 | Brabrand | A61B 8/08 600/407 |
| 2007/0293781 A1* | 12/2007 | Sims | A61B 5/02055 600/534 |
| 2011/0060215 A1 | 3/2011 | Tupin, Jr. et al. | |
| 2011/0130800 A1* | 6/2011 | Weinstein | A61B 8/4254 607/17 |
| 2012/0029375 A1 | 2/2012 | Lane et al. | |
| 2017/0245797 A1 | 8/2017 | Quinn | |
| 2018/0125444 A1 | 5/2018 | Kahlman et al. | |
| 2018/0153506 A1 | 6/2018 | Rodriquez | |
| 2018/0292523 A1 | 10/2018 | Orenstein et al. | |
| 2018/0333103 A1* | 11/2018 | Bardan | A61B 5/7289 |
| 2019/0015048 A1 | 1/2019 | Baker | |
| 2020/0253578 A1* | 8/2020 | Chae | A61B 8/4483 |

FOREIGN PATENT DOCUMENTS

| | | |
|---|---|---|
| GB | 2166871 A | 5/1986 |
| WO | 2018122661 A1 | 7/2018 |

OTHER PUBLICATIONS

Yilmaz, T., et al. "Detecting Vital Signs with Wearable Wireless Sensors." Sensors 2010, 10, p. 10837-10862, Dec. 2, 2010.

Zheng, Y., et al., "Unobtrusive Sensing and Wearable Devices for Health Informatics." IEEE Transactions on Biomedical Engineering, vol. 61, No. 5, p. 1538-1554, May 2014.

* cited by examiner

VITAL SIGN DETECTION AND MEASUREMENT

INTRODUCTION

Trained medical professionals often check vital sign measurements of a patient under their care at regular intervals to monitor the status of the patient. One vital sign that is monitored is respiration rate. Respiration rate is the number of breaths a person takes per minute. The rate is usually measured when a person is at rest and involves counting the number of breaths per minute. In addition, the quality and depth of respiration such as shallow breathing or labored breathing, and the uniformity of breath may be monitored by a trained medical professional.

The measurement of respiration rate presents challenges in the low acuity areas of a healthcare facility such as a hospital. Technologies such as capnography are expensive and require a breathing tube or nasal cannula, while other technologies require uncomfortable chest straps that are prone to low sensitivity and patient movement noise. Existing solutions also tether a patient to a device with a cannula or electrical wires, and thus reduces patient mobility.

SUMMARY

In general terms, the present disclosure relates to a patient monitoring device and method. In one possible configuration and by non-limiting example, the device and method determine a vital sign measurement by a wearable patch. Various aspects are described in this disclosure, which include, but are not limited to, the following aspects.

In one aspect, a patient monitoring device includes a base, a battery mounted to the base, first and second transceivers attached to the base at opposing angles and powered by the battery to transmit pulses and receive reflected pulses, an antenna powered by the battery and configured to wirelessly transmit data acquired from the first and second transceivers, and a computing device powered by the battery and operatively coupled to the first and second transceivers and the antenna, the computing device having a processing device and a memory storing instructions that, when executed by the processing device, cause the monitoring device to determine a respiration rate by detecting a cyclical change in distance based on the reflected pulses.

In another aspect, a method of acquiring a vital sign measurement comprises transmitting pulses, detecting an impedance from reflected pulses, using the detected impedance to determine cyclical changes in a distance, and using the determined cyclical changes in the distance to determine a respiration rate.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
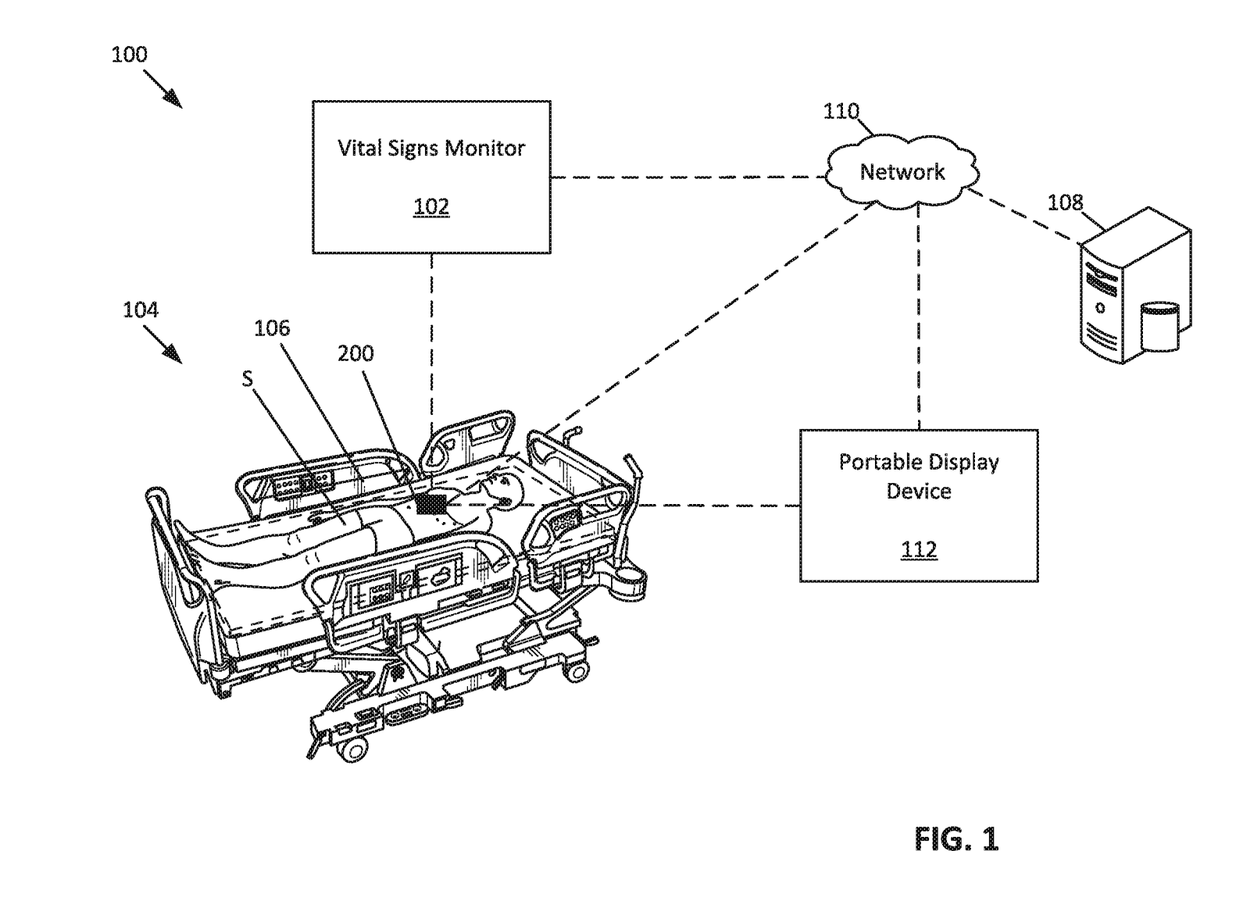
FIG. 1 schematically illustrates an example patient monitoring system.

FIG. 1 schematically illustrates an example patient monitoring system 100. The patient monitoring system 100 includes a vital signs monitor 102 configured to measure and display one or more vital signs of a subject S located in a subject arrangement area 104. The vital signs are displayed on the vital signs monitor 102 numerically, in waveform, in tabular data, in plots of tabular data, and the like. In some examples, the vital signs monitor 102 is a Connex® spot monitor available from Welch Allyn, Inc. of Skaneateles Falls, N.Y.

The subject S is a person, such as a patient, who is clinically treated by one or more medical professionals. As shown in the example of FIG. 1, the subject S is arranged in the subject arrangement area 104, which can be located inside a healthcare facility such as a hospital, medical clinic, doctor's office, etc. The subject arrangement area 104 can include a support device 106, such as a bed, on which the subject S can lie, rest, or sleep. Other examples of the support device 106 include lifts, chairs, stretchers, and surgical tables.

The patient monitoring system 100 further includes a monitoring device 200 that is configured for attachment to the chest of the subject S. The monitoring device 200 is a wireless patch that measures and monitors the respiration rate of the subject S. In one example embodiment, the monitoring device 200 is reusable after it has been used on the subject S. In another embodiment, the monitoring device 200 is disposable after it has been used.

In one example embodiment, the monitoring device 200 is operable to wirelessly communicate with the vital signs monitor 102 via a data communication network 110. In another example embodiment, the monitoring device 200 is operable to directly communicate with the vital signs monitor 102 through a wireless connection. In a further example embodiment, the monitoring device 200 is operable to directly communicate with a portable display device 112 such as a smartphone, tablet computer, laptop, and the like through another wireless connection. In these example embodiments, the respiration rate of the subject S measured by the monitoring device 200 is displayed on the vital signs monitor 102 and/or on the portable display device 112.

In further example embodiments, the monitoring device 200 is operable to wirelessly communicate with a data management system 108 via the data communication network 110. The data management system 108 operates to manage personal and/or medical information, such as health conditions and other information of the subject S. The data management system 108 can be operated by medical professionals or healthcare service providers.

The vital signs monitor 102 and portable display device 112 are also operable to communicate with the data management system 108 via the data communication network 110 to transmit data such as measured vital signs and other data associated with the subject S. In some examples, the vital signs monitor 102 and portable display device 112 are capable of directly communicating with the data management system 108.

The data management system 108 operates to provide information that can be used to assist trained medical professionals to provide suitable healthcare to the subject S. In one example embodiment, the data management system 108 may provide a connection to electronic medical record or electronic health record servers. In an alternative example embodiment, the data management system 108 may itself be an electronic medical record server or an electronic health record server. Examples of the data management system 108 include Connex® data management systems available from Welch Allyn, Inc. of Skaneateles Falls, N.Y.

The data communication network 110 communicates data between one or more computing devices, such as among the vital signs monitor 102, portable display device 112, monitoring device 200, and data management system 108. Examples of the data communication network 110 include a local area network and a wide area network, such as the Internet. The data communication network 110 includes a wireless communication system, a wired communication system, or a combination of wireless and wired communication systems. Examples of wired communication systems can transmit data using electrical or optical signals in various possible configurations. Examples of wireless communication systems can transmit signals via electromagnetic waves such as in the form of optical signals or radio frequency (RF) signals.

A wireless communication system can include an optical or RF transmitter for transmitting optical or RF signals, and an optical or RF receiver for receiving optical or RF signals. Examples of wireless communication systems include Wi-Fi communication devices that utilize wireless routers or wireless access points, cellular communication devices that utilize one or more cellular base stations, Bluetooth, ANT, ZigBee, medical body area networks, personal communications service (PCS), wireless medical telemetry service (WMTS), and other wireless communication devices and services.

Figure 2:
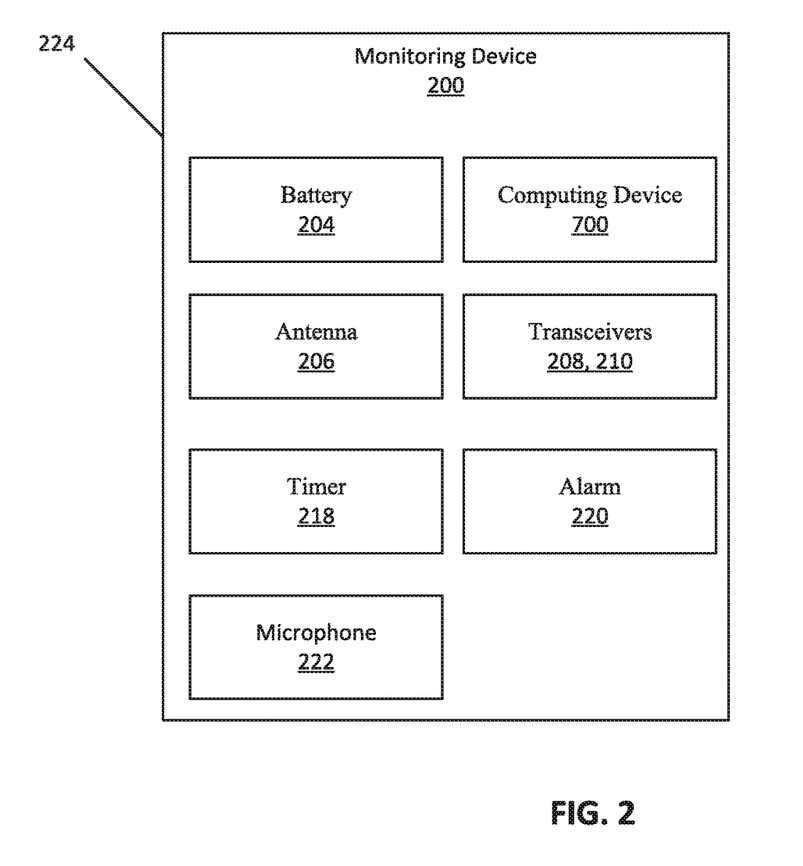
FIG. 2 is a schematic block diagram illustrating an example monitoring device.

FIG. 2 is a schematic block diagram illustrating the monitoring device 200 for detecting and measuring respiration rate. The monitoring device 200 includes a battery 204, an antenna 206, first and second transceivers 208, 210, a timer 218, and an alarm 220 that are each operatively coupled to a computing device 700. The computing device 700 includes at least a processor and a memory. The computing device 700 is described with reference to FIG. 7.

As shown in FIG. 2, the components of the monitoring device 200 including the battery 204, antenna 206, first and second transceivers 208, 210, timer 218, and alarm 220 are packaged together within a housing 224. The housing 224 is configured to environmentally protect these components when the monitoring device 200 is worn by the subject S. The housing 224 can be made from a durable, lightweight material such as plastic.

The battery 204 powers the computing device 700, antenna 206, first and second transceivers 208, 210, timer 218, and alarm 220. The battery 204 can be a replaceable and/or disposable battery. Alternatively, the battery 204 can be a rechargeable battery.

In one example embodiment, the antenna 206 is operable to wirelessly transmit data from the first and second transceivers 208, 210 to the vital signs monitor 102, portable display device 112, and/or data management system 108 via the data communication network 110.

In another example embodiment, the antenna 206 is operable to wirelessly transmit data from the first and second transceivers 208, 210 directly to the vital signs monitor 102 and/or directly to portable display device 112. In this example, the antenna 206 can be configured as a near-field communication (NFC) antenna to wirelessly transmit the data.

The first and second transceivers 208, 210 are piezo crystal oscillators that are operable to transmit pulses for measuring respiration rate. The pulses measure a distance between a chest wall and a lung cavity of the subject S, which changes when the subject S breathes due to the lung cavities filling and expanding with air. In one example embodiment, the pulses are ultrasonic. In this example embodiment, acoustic impedance (e.g., a measure of the opposition to the acoustic flow resulting from the pulses) is detected from reflected pulses, and is used to measure the respiration rate of the subject S. Other types of pulses, such as radio frequency pulses and/or electrical pulses, could also be used.

The timer 218 alternates the operation of the monitoring device 200 between a sleep mode and an active mode. In the sleep mode, energy from the battery 204 is conserved. The timer 218 automatically wakes up the monitoring device 200 from the sleep mode to operate under the active mode at predetermined time intervals. When in the active mode, the first and second transceivers 208, 210 transmit pulses for a predetermined number of cycles to measure and/or monitor the respiration rate of the subject S. By alternating between the sleep and active modes, the monitoring device 200 preserves the life of the battery 204.

The alarm 220 is configured to generate a signal when the data acquired from the first and second transceivers 208, 210 indicates that the respiration rate of the subject S is too low or too high, or that a trend of respiration rates indicates an impending adverse event. An algorithm can be used to analyze the data acquired from the first and second transceivers 208, 210 to generate the signal. In one example, the alarm 220 is an audible alarm such as a beeping noise. In another example, the alarm 220 is a visual alarm such as a blinking light.

In one example embodiment, the monitoring device 200 includes a microphone 222 that detects whether the subject S is talking. Talking affects respiration rate because a person is not able to talk and breathe at the same time. Thus, the microphone 222 can reduce false alarms. The microphone is operatively coupled to the computing device 700. In one example, when the microphone 222 detects that the subject S is talking, the microphone 222 causes the monitoring device 200 to operate in the sleep mode, such that the first and second transceivers 208, 210 do not transmit the pulses used to measure and/or monitor the respiration rate of the subject S. Thus, the microphone preserves the life of the battery 204 when the subject S is talking.

In further example embodiments, the microphone 222 is configured to distinguish between regular talking, and other audible sounds made by the subject S such as snoring while sleeping or moaning when in pain. By distinguishing these audible sounds, the monitoring device 200 remains in the active mode when the subject S is sleeping or in pain.

Figure 3:
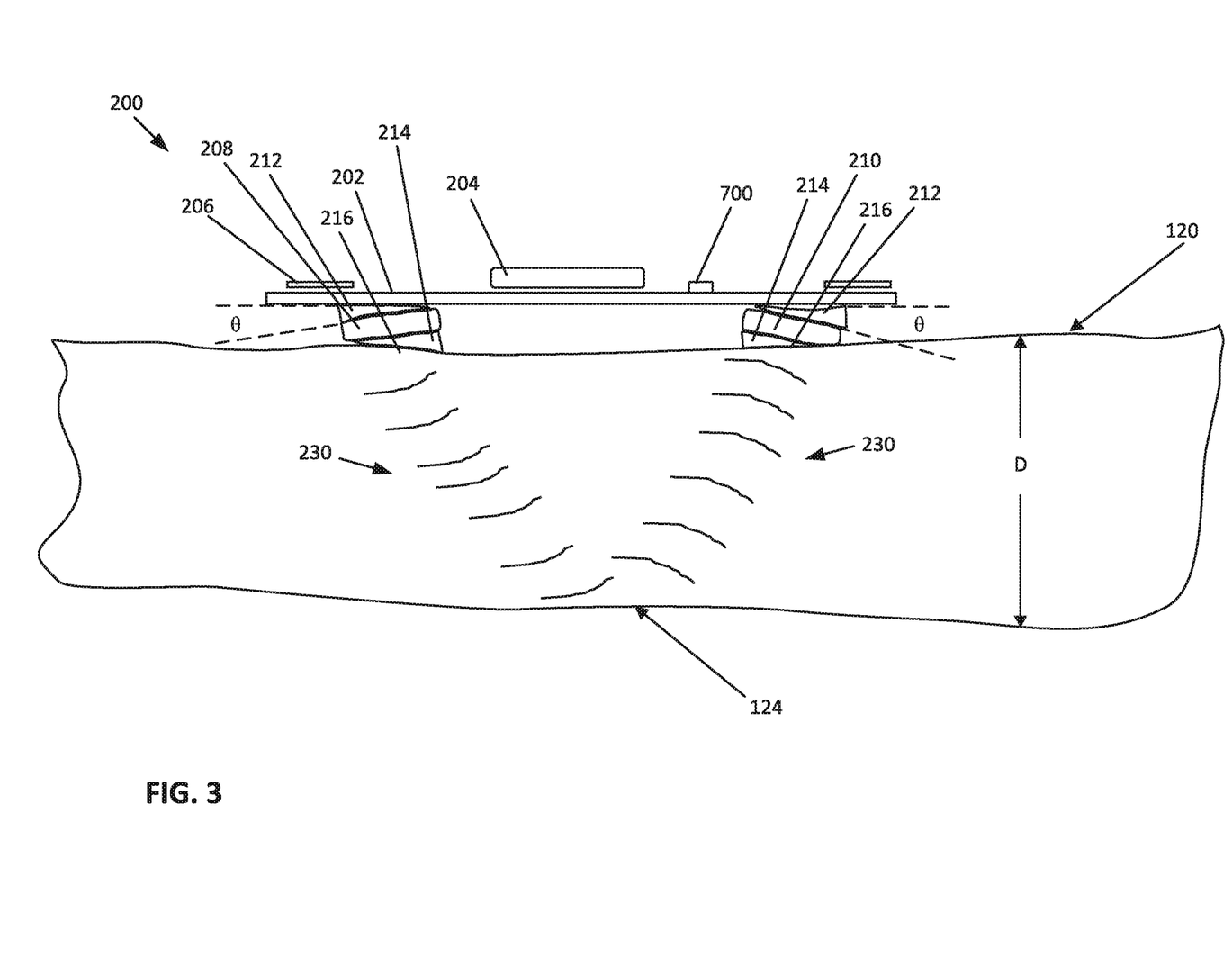
FIG. 3 is a cross-sectional view of an example monitoring device.

FIG. 3 is a cross-sectional view of the monitoring device 200 attached to the chest wall 120 of the subject S. The first and second transceivers 208, 210 are each configured to transmit and receive pulses 230 that reflect off the lung cavity 124 for measuring a distance D between the chest wall 120 and the lung cavity 124 (e.g., the thickness of the chest cavity). The pulses 230 transmitted and received by the first and second transceivers 208, 210 provide a robust signal that can be measured while the monitoring device 200 is worn by the subject S.

The distance D (e.g., the thickness of the chest cavity) is at a maximum distance $D_{max}$ when the subject S exhales such that the lung cavity 124 deflates. The distance D is at a minimum distance $D_{min}$, when the subject S inhales such that the lung cavity inflates with air. The respiration rate of the subject S is determined by measuring the cycles between the maximum distance $D_{max}$ and minimum distance $D_{min}$. Additionally, by measuring the maximum distance $D_{max}$ and minimum distance $D_{min}$, the quality and depth of respiration such as shallow breathing or labored breathing, and the uniformity of breath are also monitored.

As shown in FIG. 3, the monitoring device 200 includes a base 202 that supports the battery 204, antenna 206, and first and second transceivers 208, 210. The base 202 is a sheet of durable material. In one example embodiment, the base 202 is made from plastic. Alternative materials such as lightweight aluminum may also be used for the base 202.

A positioning wedge 212, gel layer 214, and adhesive layer 216 are included for each of the first and second transceivers 208, 210. When the monitoring device 200 is worn, these components are positioned between the base 202 and the chest wall 120 of the subject S.

The positioning wedges 212 mount the first and second transceivers 208, 210 to the base 202 at opposing angles θ such that the pulses 230 emitted from one of the first and second transceivers 208, 210 reflect off the lung cavity 124 at an angle, and the reflected pulses 230 are received by the other of the first and second transceivers 208, 210. The acoustic impedance of the lung cavity 124 (e.g., a measure of the opposition that the lung cavity 124 presents to the acoustic flow resulting from the pulses 230) is detected from the reflected pulses 230, and is used to determine the distance D between the chest wall 120 and the lung cavity 124.

In example embodiments, the positioning wedges 212 mount the first and second transceivers 208, 210 at opposing angles θ in a range from about 30° to about 60°. In one example embodiment, the opposing angles θ are about 45°.

The positioning wedges 212 allow both the first and second transceivers 208, 210 to be mounted to the chest wall 120 of the subject S (as opposed to having one transceiver mounted to the chest wall and the other to the back of the subject S). By mounting both the first and second transceivers 208, 210 to the chest wall 120, the number of interfaces (e.g., the organs, tissues, muscles, etc.) that the pulses 230 go through is reduced, and thus signal loss and noise are reduced. Thus, the first and second transceivers 208, 210 provide a robust signal that can be measured while the monitoring device 200 is worn by the subject S, including when the subject S is active such as when the subject S walking while wearing the monitoring device 200.

The positioning wedges 212 are made from a soft polymeric material that allows the monitoring device 200, including the first and second transceivers 208, 210, to conform to the shape and contours of the chest wall 120 of the subject S.

The gel layer 214 is applied over the first and second transceivers 208, 210. The gel layer 214 improves the transfer of the pulses 230 from the first and second transceivers 208, 210 to the chest wall 120 and lung cavity 124 of the subject S. In one example embodiment, the gel layer 214 is an ultrasound gel pre-contained within a septic container. After the monitoring device 200 has been used on the subject S, the septic container containing the ultrasound gel can be discarded so that the monitoring device 200 is partially disposable and/or reusable.

The adhesive layer 216 is applied over the gel layer 214. The adhesive layer 216 attaches the monitoring device 200 to the chest wall 120 of the subject S. The adhesive layer 216 is a thin, flexible sheet of material that is sticky on one or both sides. The adhesive layer 216 can be a woven fabric, plastic, or latex strip that includes an acrylate adhesive. In one example embodiment, the adhesive layer 216 is disposable along with the gel layer 214.

Figure 4:
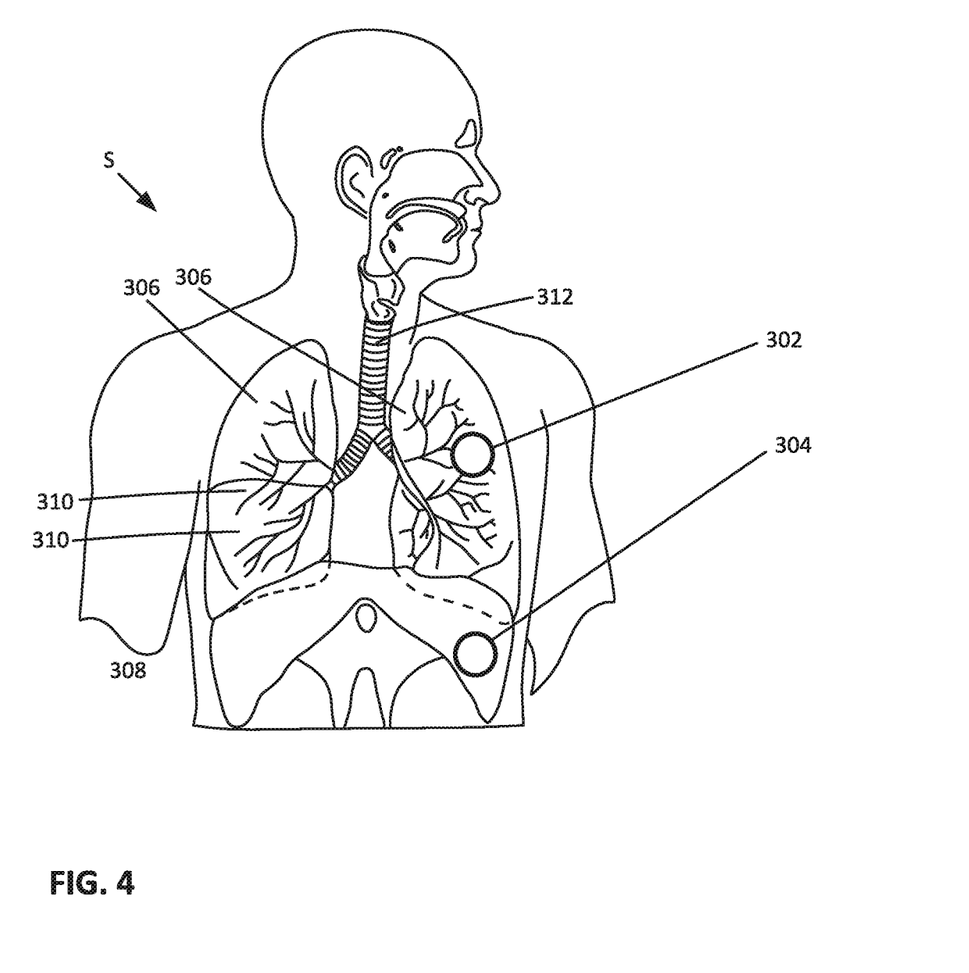
FIG. 4 illustrates exemplary placements for an example monitoring device.

FIG. 4 illustrates example placements for the monitoring device 200 on the subject S. In one example embodiment, the monitoring device 200 can be placed in a first location 302 that is over the lung cavities 306 of the subject S. In another example embodiment, the monitoring device 200 can be placed in a second location 304 that is over the diaphragm 308 of the subject S. FIG. 3 further shows the airways 310 and trachea 312 of the subject S.

Figure 5:
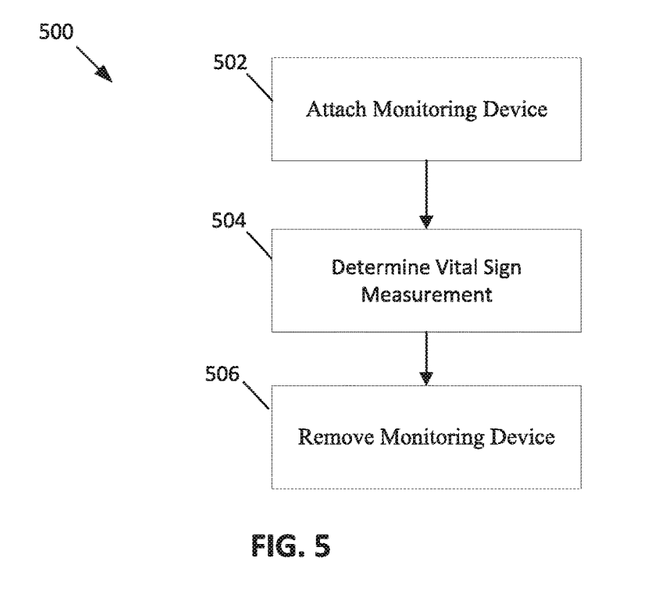
FIG. 5 illustrates an example method of acquiring a vital sign measurement.

FIG. 5 illustrates a method 500 of acquiring a vital sign measurement. The method 500 includes attaching a monitoring device to a chest wall of a subject (Step 502), determining a vital sign measurement (Step 504), and removing the monitoring device from the patient.

In Step 502, the monitoring device is a wireless device, and is attached to the chest wall of the subject using a disposable adhesive. The monitoring device is worn by the subject without requiring a breathing tube or nasal cannula, or any type of tether such as an electrode attached to an end of a cable. The subject is mobile such that the subject is able to freely walk about a healthcare facility with the monitoring device attached to the subject. The monitoring device is worn by the subject for a period of time up to 5 days.

In Step 504, determining a vital sign measurement includes determine a respiration rate of the subject. Additionally, determining a vital sign measurement can include determining the quality and depth of respiration, and the uniformity of breath. The step of determining a vital sign measurement (Step 504) is described in more detail with reference to FIG. 6

In Step 506, the monitoring device is removed from the subject by detaching the disposable adhesive from the chest wall of the subject. In some example embodiments, the monitoring device is a disposable device that is discarded after use. In other example embodiments, the monitoring device is reusable. In further example embodiments, certain components, such as the gel layer 214 and adhesive layer 216, are disposable while other components such as the first and second transceivers 208, 210 are reusable.

Figure 6:
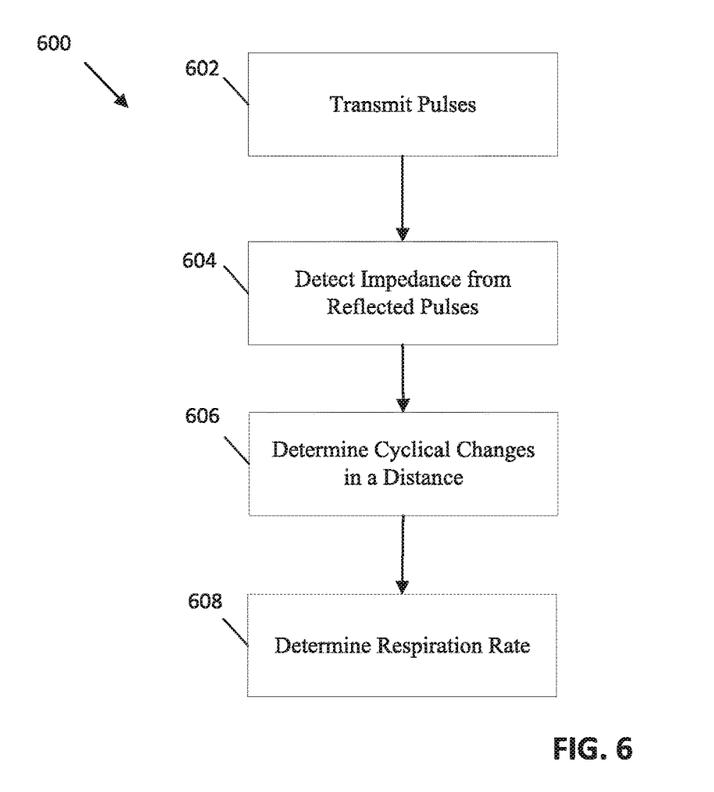
FIG. 6 illustrates an example method of determining a vital sign measurement.

FIG. 6 illustrates an example method of determining a vital sign measurement (i.e., Step 504 in the method 500). The method 600 includes transmitting pulses (Step 602), detecting an impedance from reflected pulses (Step 604), using the detected impedance to determine cyclical changes in a distance (Step 606), and using the determined cyclical changes in the distance to determine a respiration rate (Step 608).

In Step 602, a first transceiver of a monitoring device transmits pulses. In one example, the pulses are ultrasonic pulses that are transmitted through an ultrasonic gel.

Next, in Step 604, a second transceiver of the monitoring device receives the reflected pulses and an impedance is detected from reflected pulses. In one example, the impedance is an acoustic impedance. The first and second transceivers are mounted at opposing angles such that the pulses are transmitted at a first angle, the reflected pulses are received at a second angle, and the first and second angles intersect. In one example embodiment, the pulses from the first transceiver are transmitted through a chest wall, and the pulses received from the second transceiver are reflected from a lung cavity. In alternative example embodiments, the pulses are transmitted by the second transceiver and the reflected pulses are received by the first transceiver. In further example embodiments, the first and second transceivers alternate between transmitting and receiving the pulses, and thus operate as both transmitters and receivers.

In yet other embodiments, measurements other than acoustic impedance can be used. For example, measuring a difference in time for each pulse can be used, similar to what is done in ultrasound technology.

In Step 606, the detected impedance is used to determine cyclical changes in a distance. In an example embodiment, the distance is between a chest wall and a lung cavity. The distance is at a maximum during exhalation when the lung cavity is deflated. The distance is at a minimum during inhalation when the lung cavity is inflated with air.

Figure 7:
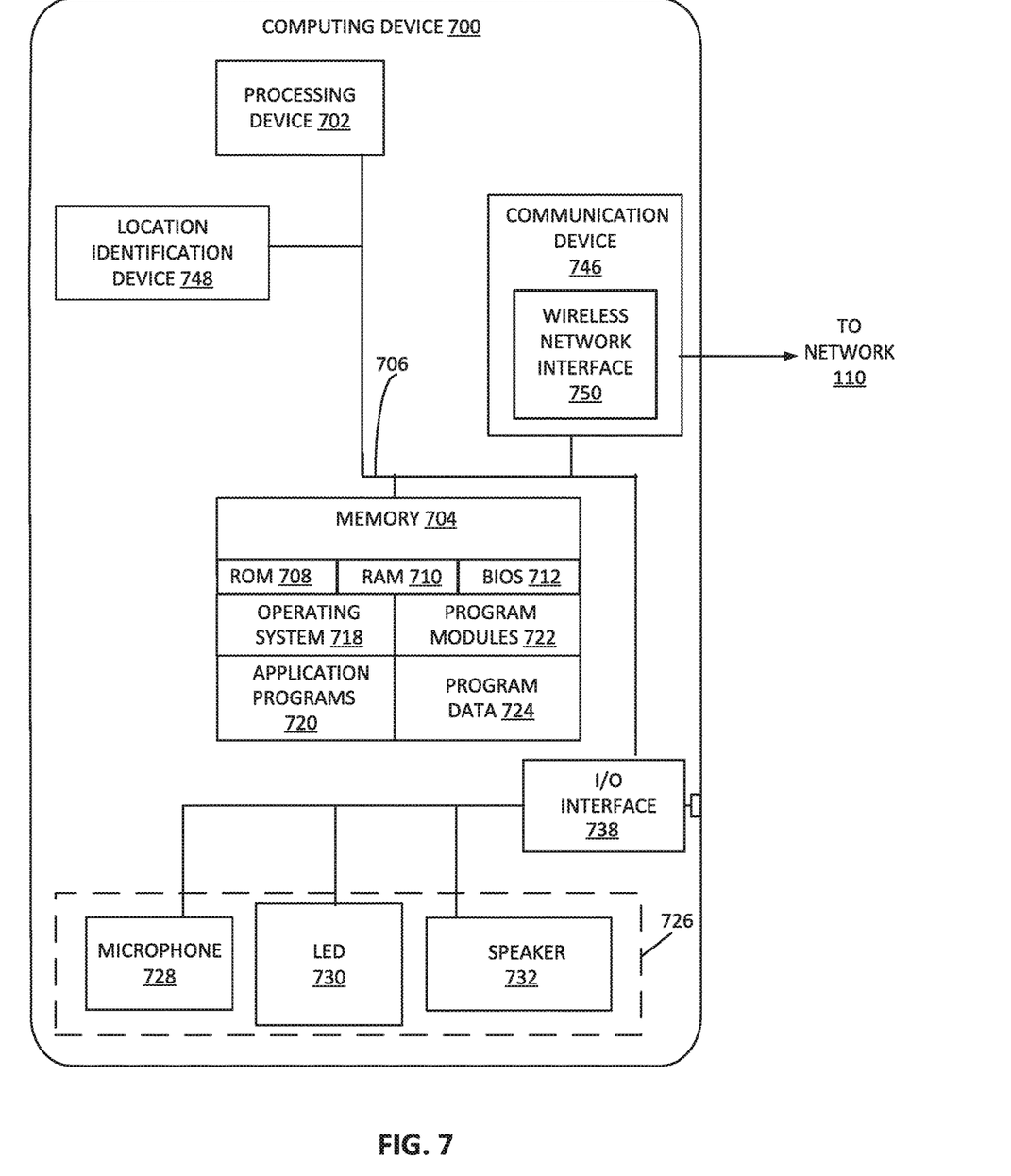
FIG. 7 illustrates an exemplary architecture of a computing device that can be used to implement aspects of the present disclosure.

In Step 608, the determined cyclical changes in the distance to determine a respiration rate. In a further example, a quality and depth of respiration is determined by measuring the maximum distance and the minimum distance between the chest wall and the lung cavity FIG. 7 illustrates an exemplary architecture of the computing device 700 that can be used to implement aspects of the present disclosure, including the monitoring device 200. The computing device 700 is used to execute the various functions, methods, or operations described herein. The monitoring device 200 can include all or some of the elements described with reference to FIG. 7, with or without additional elements.

The computing device 700 includes at least one processing device 702, such as a central processing unit (CPU). The computing device 700 also includes a memory 704, and a bus 706 that couples various system components including the memory 704 to the processing device 702. The bus 706 can be of a variety of bus architectures.

The memory 704 may include read only memory 708 and random access memory 710. A basic input/output system 712 containing the basic routines that act to transfer information within the computing device 700 is typically stored in the read only memory 708. A number of program modules can be stored in the memory 704, including an operating system 718, one or more application programs 720, other program modules 722, and program data 724.

In some embodiments, the computing device 700 includes various input and peripheral devices 726 such as a microphone 728, Light-Emitting Diodes (LED) 730, and speaker 732. Other embodiments may include additional or fewer input and peripheral devices. The input and peripheral devices 726 are connected to the processing device 702 through an input/output interface 738 that is coupled to the bus 706. In accordance with the example embodiments described above, the microphone 728 can be used by the computing device 700 to detect whether a subject is talking to reduce false alarms when measuring respiration rate. The LEDs 730 and speaker 732 can be part of the alarm 220 (see FIG. 2) that generates a visual or audible alert when an abnormal respiration rate is measured.

The computing device 700 further includes a communication device 746 configured to establish communication across a network such as the data communication network 110 (see FIG. 1). In some embodiments, the computing device 700 is connected to the network through a network interface, such as a wireless network interface 750.

In yet other embodiments, the communication device 746 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 700 typically includes at least some form of computer-readable media. Computer readable media includes any available media that can be accessed by the computing device 700. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, or any other medium that can be used to store the desired information and that can be accessed by the computing device 700. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wireless media such as acoustic, radio frequency, infrared, and other wireless media. Combinations of any of the above are also included within the scope of computer readable media.

The computing device 700 is an example of programmable electronics, which may include one or more computing devices, and when multiple computing devices are included, such computing devices can be coupled together with a suitable data communication network so as to collectively perform the various functions, methods, or operations disclosed herein.

The computing device 700 can include a location identification device 748. The location identification device 748 is configured to identify the location or geolocation of the computing device 700. The location identification device 748 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

The systems and method described herein result in a significant technical advantage. For example, the monitoring device 200 more efficiently captures vital sign measurements including respiration rate, quality and depth of respiration, and the uniformity of breath. Also, the monitoring device 200 determines vital sign measurements more accurately and in less time.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features.

Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A monitoring device for detecting and measuring a respiration rate of a subject, comprising:

a base;

a battery mounted to the base;

first and second transceivers attached to the base at opposing angles, and powered by the battery to transmit ultrasonic pulses and receive reflected ultrasonic pulses;

an antenna powered by the battery, and configured to wirelessly transmit data acquired from the first and second transceivers;

a microphone configured to detect when the subject is talking; and a computing device powered by the battery, and operatively coupled to the first and second transceivers and the antenna, the computing device having a processing device and a memory storing instructions that, when executed by the processing device, cause the processing device to:

determine the respiration rate by detecting a cyclical change in distance based on the reflected ultrasonic pulses; and when the microphone detects the subject is talking, cause the first and second transceivers to operate under a sleep mode causing the first and second transceivers to stop transmitting the ultrasonic pulses, and when the microphone does not detect the subject is talking, causing the first and second transceivers to transmit the ultrasonic pulses for determining the respiration rate of the subject.

2. The monitoring device of claim 1, further comprising a timer configured to alternate an operation of the monitoring device between the sleep mode and an active mode, wherein the timer automatically changes from the sleep mode to operate under the active mode at predetermined time intervals.

3. The monitoring device of claim 1, further comprising an alarm configured to generate an alert when the data acquired from the first and second transceivers indicates that the respiration rate is below or above a threshold.

4. The monitoring device of claim 1, wherein the cyclical change in distance detected by the monitoring device is between a chest wall and a lung cavity.

5. The monitoring device of claim 4, wherein the processing device detects acoustic impedance from the reflected ultrasonic pulses to measure the respiration rate.

6. The monitoring device of claim 5, wherein the first and second transceivers detect a maximum distance when the subject exhales, the first and second transceivers detect a minimum distance when the subject inhales, and the processing device determines the respiration rate by measuring cycles between the maximum distance and the minimum distance.

7. The monitoring device of claim 6, wherein the processing device is further configured to determine a quality and depth of respiration and a uniformity of breathe by measuring the maximum distance and the minimum distance.

8. The monitoring device of claim 1, further comprising a gel layer applied over the first and second transceivers.

9. The monitoring device of claim 8, wherein the gel layer is an ultrasound gel pre-contained within a septic container.

10. The monitoring device of claim 9, further comprising an adhesive layer applied over the gel layer, the adhesive layer configured to attach to a chest wall.

11. The monitoring device of claim 10, wherein the gel layer and adhesive layer are disposable, and the first and second transceivers are reusable.

12. The monitoring device of claim 1, wherein the monitoring device is disposable.

* * * * *